(12) United States Patent
Lan et al.

(10) Patent No.: US 9,345,654 B2
(45) Date of Patent: May 24, 2016

(54) HAIR DYE PRODUCT

(71) Applicant: NATURAL MEDICINE INSTITUTE OF ZHEJIANG YANGSHENGTANG CO., LTD., Zhejiang (CN)

(72) Inventors: Hongying Lan, Zhejiang (CN); Liu Hu, Zhejiang (CN)

(73) Assignee: NATURAL MEDICINE INSTITUTE OF ZHEJIANG YANGSHENGTANG CO., LTD., Hangzhou (CN)

( * ) Notice: Subject to any disclaimer, the term of this patent is extended or adjusted under 35 U.S.C. 154(b) by 0 days.

(21) Appl. No.: 14/422,589

(22) PCT Filed: Aug. 23, 2013

(86) PCT No.: PCT/CN2013/082122
§ 371 (c)(1),
(2) Date: Feb. 19, 2015

(87) PCT Pub. No.: WO2014/029352
PCT Pub. Date: Feb. 27, 2014

(65) Prior Publication Data
US 2015/0231050 A1    Aug. 20, 2015

(30) Foreign Application Priority Data
Aug. 24, 2012 (CN) .......................... 2012 1 0302425

(51) Int. Cl.
| | | |
|---|---|---|
| *A61Q 5/10* | (2006.01) | |
| *A61K 8/49* | (2006.01) | |
| *A61K 8/60* | (2006.01) | |
| *A61K 8/97* | (2006.01) | |

(52) U.S. Cl.
CPC ................ *A61K 8/498* (2013.01); *A61K 8/602* (2013.01); *A61K 8/97* (2013.01); *A61Q 5/10* (2013.01); *A61K 2800/592* (2013.01); *A61K 2800/882* (2013.01); *A61K 2800/884* (2013.01)

(58) Field of Classification Search
CPC ........... A61Q 5/10; A61K 8/602; A61K 8/97; A61K 2800/592; A61K 2800/884; A61K 2800/882
USPC ........................................................... 8/405
See application file for complete search history.

(56) References Cited

U.S. PATENT DOCUMENTS

| | | | |
|---|---|---|---|
| 2003/0145395 A1 | 8/2003 | Murakami | |
| 2007/0251024 A1 | 11/2007 | Greaves et al. | |
| 2009/0249563 A1* | 10/2009 | Greaves .................. | A61K 8/19 8/405 |

FOREIGN PATENT DOCUMENTS

| | | |
|---|---|---|
| CN | 1462184 A | 12/2003 |
| CN | 1478459 A | 3/2004 |
| CN | 1561950 A | 1/2005 |
| CN | 101164528 A | 4/2008 |
| CN | 101431976 A | 5/2009 |
| CN | 101869536 A | 10/2010 |
| CN | 102198058 A | 9/2011 |
| WO | 2011/078158 A1 | 6/2011 |
| WO | 2014/029352 A1 | 2/2014 |

OTHER PUBLICATIONS

*Hygiene and Safety General Requirements of Cosmetics* (issued by the Ministry of Health of the People's Republic of China and Standardization Administration of the People's Republic of China, 2011).
Tan Guo-jin et al., *Current Research Situation of Natural Edible Plant-pigment and its Prospect*, College of Chemistry and Chemical Engineering, Dec. 31, 2005.
International Search Report corresponding to the PCT/CN2013/082122 application.

* cited by examiner

*Primary Examiner* — Eisa Elhilo

(57) ABSTRACT

The invention relates to a hair dye product, in particular to a hair dye product comprising at least two natural dye substances, and the use of the at least two natural dye substances in human or animal hair dyeing or in preparation of hair dye product for human or animal, wherein at least one of the natural dye substances displays yellow or yellowish brown color series; preferably, the natural dye substance displaying the yellow or yellowish brown color series is selected from quercetin or a derivative thereof, or an extract containing the quercetin or the derivative thereof, or a mixture thereof. The at least two natural dye substances of the invention are combined as dyeing ingredient, compared with those used alone, the range of the color is very different, and the color of the dyed hair is natural, which is yellowish black and consistent with human real hair, moreover, the hair dyeing effect is stable and the color is not easy to fade.

18 Claims, No Drawings

HAIR DYE PRODUCT

CROSS REFERENCE TO RELATED APPLICATIONS

This application is the National Stage of International Application No. PCT/CN2013/082122, filed Aug. 23, 2013, which claims priority to Chinese Application No. 201210302425.9, filed Aug. 24, 2012, which are incorporated by reference herein in their entirety.

TECHNICAL FIELD

The invention belongs to the field of daily chemicals, relates to a hair dye product, specifically relates to a hair dye product comprising at least two natural dye substances, and the use of the at least two natural dye substances in hair dye product.

BACKGROUND OF THE INVENTION

With the improvement of people's living level, hair-dyeing has become a way of pursuing fashion and beauty. At present, commercially available hair dyes can be divided into three classes according to raw materials: 1) chemically synthesized hair dyes which account for a major market share, wherein harmful substances such as p-phenylenediamine, hydrogen peroxide and the like are added; 2) chemically synthesized hair dyes with "natural" concepts which account for a small market share, wherein some plant-based conceptual components are added and the p-phenylenediamine and the like are also contained; and 3) natural hair dyes which account for a very small market share. The first two classes of hair dyes are convenient and quick to use, but have greater allergenicity and potential carcinogenicity, and can cause hair damage. Although the natural hair dyes available on the market are safe and non-irritating, natural hair dye components are large molecules and difficult to color hair, therefore the dyeing effect and the convenience of use are still unsatisfactory.

Many natural hair dye products are reported in documents, for example, those as mentioned in CN101869536A (Chinese Patent Application No.: 201010207891.X, Publication Date: Oct. 27, 2010), CN1561950 (Chinese Patent Application No.: 20041003087.0, Publication Date: Jan. 12, 2005) and CN101164528 (Chinese Patent Application No.: 200710133376.X, Publication Date: Apr. 23, 2008), and according to preparation and use methods mentioned in embodiments therein, these natural hair dye products are found to be capable of dyeing white hair into a purple or deep purple black color. As another example, according to the preparation and use methods mentioned in the embodiment of CN1478459A (Chinese Patent Application No.: 03119171.1.3, Publication Date: Mar. 3, 2004), the white hair can be dyed into a yellowish brown color. The hair colored with these natural hair dye products is greatly different from the real hair of human and the color is very unnatural; and in another example, according to the preparation and use methods mentioned in the embodiment of CN102198058A (Chinese Patent Application No.: 201010132584.X, Publication Date: Sep. 28, 2011), the white hair can be dyed into a brownish grey-black color. However the dyed hair has poor fastness, and moreover, henna has carcinogenicity and is prohibited in accordance with *Hygiene and Safety General Requirements of Cosmetics* (issued by the Ministry of Health of the People's Republic of China and Standardization Administration of the People's Republic of China, 2011 edition).

These problems mentioned above lead to the poor acceptance of the existing natural hair dyes among consumers. Therefore, there is an urgent need, for those skilled in the art, to develop a natural hair dye, particularly a natural black dye, which is safe, non-toxic, non-irritating, simple and convenient to operate, easy to dye and natural in color.

Contents of the Invention

The invention aims at overcoming the shortcomings of existing hair dye agents as mentioned above and providing a natural black dye product, which is safe, non-toxic, non-irritating, convenient to operate, easy to dye, natural in color, good in fastness, etc.

The first aspect of the invention relates to a product for human or animal hair dyeing, comprising an effective amount of natural dye substance, and optionally excipients which are acceptable in hair dye product, wherein the said natural dye substance comprises at least two kinds of substances, and displays at least two color series, wherein a new color is produced by the superposition of the color series, wherein at least one of the natural dye substance displays yellow or yellowish brown color series; preferably, the natural dye substance displaying the yellow or yellowish brown color series is selected from quercetin or the derivative thereof, an extract containing the quercetin or the derivative thereof, and a mixture thereof.

In one embodiment of the invention, the new color refers to the color series which is close to the natural hair color of human (in particular to Asians), such as yellowish black color series.

In one embodiment of the invention, the natural dye substance displaying the yellow or yellowish brown color series, is selected from the quercetin or the derivative thereof, the extract containing the quercetin or the derivative thereof, and a mixture thereof, and displays the yellow or yellowish brown color series by itself or after forming complex with a metal salt; the quercetin derivative is such as rutin, polystachoside, neoisorutin, guaijaverin or quercitroside; and the extract containing the quercetin or the derivative thereof is a plant extract in which quercetin is the maincomponent, such as a sophora japonica flower-bud extract or a sophora japonica flower extract.

The product according to the first aspect of the invention, at least one of the natural dye substances displays a color series rather than the yellow or yellowish brown color series, such as purple or purple-black color series, or blue or blue-black color series; preferably, the natural dye substance displaying a color series rather than the yellow or yellowish brown color series is selected from plant polyphenols and other natural dyes; preferably, the plant polyphenols are such as gallic acid, hematoxylin, tea polyphenols, apple polyphenols, gallnut extract, pomegranate rind extract, gingko leaf extract or giant knotweed extract; preferably, the other natural dyes are for example indigo, gardenia blue, cocoa pigment, purple sweet potato pigment, purple cabbage pigment, or algae blue pigment; or the natural dye substnace displaying the color series rather than the yellow or yellowish brown color serie is a mixture of plant polyphenols and other natural dye substances; and the natural substance itself or after forming complex with a metal salt displays the purple or purple-black color series or the blue or blue-black color series.

In one embodiment of the invention, by compounding the natural dye substance displaying the yellow or yellowish brown color series with the natural dye substance displaying the purple or purple-black color series or the blue or blue-black color series, the color series which is close to the natural hair color of human (in particular to Asians), such as the yellowish black color series can be obtained by color superposition.

The product according to the first aspect of the invention, the content of the natural dye substance accounts for 0.05-20% of the total weight of the hair dye product, preferably 0.5-15%, and more preferably 1-10%.

In the invention, the proportion between the natural dye substances forming different color series is not particularly limited, and those skilled in the art can adjust the proportion according to practical needs. For example, if people would like to have darker hair colors, the amount of the natural dye substance displaying the blue-black or purple-black color series should be increased; and if people would like to have yellower hair colors, the amount of the natural dye substance displaying the yellow or yellowish brown color series should be increased.

In one embodiment of the invention, the content of the natural dye substance displaying the yellow or yellowish brown color series accounts for 0.02-2% of the total weight of the hair dye product, such as 0.05-1.5%, such as 0.1-0.6%; and the content of the natural dye substance displaying the blue-black or purple-black color series accounts for 0.01-15% of the total weight of the hair dye product, such as 0.5-12%, such as 1-7%.

The product according to the first aspect of the invention, it further comprises a metal salt. When the natural dye substance is a plant polyphenol, it forms a complex with the metal salt. Therefore, when the natural dye substance is a plant polyphenol, the yellow or yellowish brown color series, the purple or purple-black color series, or the blue or blue-black color series refers to the color displayed by the plant polyphenol itself or after forming the complex with the metal salt.

In the invention, the metal salt is divalent. In one embodiment of the invention, the metal salt is a ferrous salt. The ferrous salt is selected from one of ferrous sulfate, ferrous nitrate, ferrous gluconate, ferrous lactate, ferrous fumarate and etc., or is a mixture of any two or more of the above substances.

In the invention, the content of the metal salt accounts for 0.05-20% of the total weight of the hair dye product, preferably 0.5-15%, and more preferably 1%-12%.

The product according to the first aspect of the invention, the acceptable excipients in the hair dye product comprise penetration enhancer, antioxidant, preservative, disulfide bond reducing agent, alkalizer or thickener and etc. Those skilled in the art can select one or more according to the practical needs and the suitable dose.

The second aspect of the invention relates to a combined product for human or animal hair dyeing, which comprises a softening preparation, a dye preparation and a mordant preparation, wherein the dye preparation comprises an effective amount of natural dye substance, which comprises at least two kinds of substances and displays at least two color series, wherein a new color is produced by the superposition of the color series, wherein at least one of the natural dye substances displays yellow or yellowish brown color series; preferably, the natural dye substance displaying the yellow or yellowish brown color series is selected from the group consisting of quercetin or the derivative thereof, an extract containing the quercetin or the derivative thereof, and a mixture thereof.

In one embodiment of the invention, the new color refers to the color series which is close to the natural hair color of human (in particular to Asians), such as a yellowish black color series.

In one embodiment of the invention, the natural dye substance displaying the yellow or yellowish brown color series is selected from the group consisting of the quercetin or the derivative thereof, the extract containing the quercetin or the derivative thereof, and a mixture thereof, and displays the yellow or yellowish brown color series by itself or after forming complex with a metal salt; the quercetin derivative is such as rutin, polystachoside, neoisorutin, guaijaverin or quercitroside; and the extract containing the quercetin or the derivative thereof is a plant extract in which the quercetin is the main component, such as a sophora japonica flower extract or a sophora japonica flower-bud extract.

The combined product according to the second aspect of the invention, at least one of the natural dye substances displays a color series rather than the yellow or yellowish brown color series, such as a purple or purple-black color series, or a blue or blue-black color series; preferably, the natural dye substance displaying the color series rather than the yellow or yellowish brown color series is selected from the group consisting of plant polyphenols and other natural dyes; preferably, the plant polyphenols are such as gallic acid, hematoxylin, tea polyphenols, apple polyphenols, gallnut extract, pomegranate rind extract, gingko leaf extract or giant knotweed extract; preferably, the other natural dyes are such as indigo, gardenia blue, cocoa pigment, purple sweet potato pigment, purple cabbage pigment, algae blue pigment; or the natural dye substnace displaying the color series rather than the yellow or yellowish brown color serie is a mixture of plant polyphenols and other natural dyes; and the natural substance itself or after forming a complex with a metal salt displays the purple or purple-black color series, or the blue or blue-black color series.

In one embodiment of the invention, by compounding the natural dye substance displaying the yellow or yellowish brown color series with the natural dye substance displaying the purple or purple-black color series or the blue or blue-black color series, the color series which is close to the natural hair color of human (in particular to Asians), such as the yellowish black color series, can be obtained by color superposition.

The combined product according to the second aspect of the invention, the content of the natural dye substances accounts for 0.05-20% of the total weight of the combined product, preferably 0.5-15%, and more preferably 1-10%.

In the invention, the proportion between the natural dye substances forming different color series is not particularly limited, and those skilled in the art can adjust the proportion according to practical needs. For example, if people would like to have darker hair colors, the amount of the natural dye substance displaying the blue-black or purple-black color series should be increased; and if people would like to have the yellower hair colors, the amount of the natural dye substance displaying the yellow or yellowish brown color series should be increased.

In one embodiment of the invention, the content of the natural dye substance displaying the yellow or yellowish brown color series accounts for 0.02-2% of the total weight of the combined product, such as 0.05-1.5%, and such as 0.1-0.6%; and the content of the natural dye substance displaying the blue-black or purple-black color series accounts for 0.01-15% of the total weight of the combined product, such as 0.5-12%, and such as 1-7%.

The combined product according to the second aspect of the invention, it further comprises a metal salt. When the natural dye substance is a plant polyphenol, it forms a complex with the metal salt. Therefore, when the natural dye substance is a plant polyphenols, the yellow or yellowish brown color series, the purple or purple-black color series, or the blue or blue-black color series refers to the color displayed by the plant polyphenol itself or after forming the complex with the metal salt.

In the invention, the metal salt is divalent. In one embodiment of the invention, the metal salt is a ferrous salt. The ferrous salt is selected from one of ferrous sulfate, ferrous nitrate, ferrous gluconate, ferrous lactate, ferrous fumarate and etc., or is a mixture of any two or more of the above substances.

In the invention, the content of the metal salt accounts for 0.05-20% of the total weight of the hair dye product, preferably 0.5-15%, and more preferably 1%-12%.

The combined product according to the second aspect of the invention, the softening preparation, the dye preparation or the mordant preparation is differentiated according to different functions. In practical applications, the dye preparation can be respectively combined with the softening preparation or the mordant preparation, so that different formulations can be formed, for example, It could be in one of the following formulations:

(1) Four-preparation type: the different natural dye substances in the dye preparation are divided into a dyeing component and a color-matching component according to the color series, thereby forming four preparations, namely the softening preparation, the dye component, the color-matching component and the mordant preparation;

(2) Three-preparation type: the softening preparation, the dye preparation and the mordant preparation; or one of the dyeing component and the color-matching component is combined with the softening preparation or the mordant preparation; and (3) Two-preparation type: the dye preparation is combined with the softening preparation or the mordant preparation, for example, One of the dye component and the color-matching component is combined with the softening preparation and the other one of the dye component and the color-matching component is combined with the mordant preparation; both the dye component and the color-matching component are combined with the mordant preparation; both the dye component and the color-matching component are combined with the mordant preparation, or both the dye component and the color-matching component are combined with the softening preparation.

In the combined product according to the second aspect of the invention, the softening preparation further comprises one or more of disulfide bond reducing agent, penetration enhancer, thickener and alkalizer; and/or The dye preparation further comprises one or more of antioxidant, penetration enhancer and preservative; and/or The mordant preparation further comprises one or more of antioxidant, penetration enhancer and preservative.

The third aspect of the invention relates to an use of natural dye substance in human or animal hair dyeing or the use of the natural dye substance in preparation of a product for human or animal hair dyeing, wherein the natural dye substance comprises at least two kinds of substances and displays at least two color series, wherein a new color is produced by the superposition of the color series, wherein at least one of the natural dye substances displays yellow or yellowish brown color series; preferably, the natural dye substance displaying the yellow or yellowish brown color series is selected from quercetin or the derivative thereof, an extract containing the quercetin or the derivative thereof, and a mixture thereof.

In one embodiment of the invention, the new color refers to the color series which is close to the natural hair color of human (in particular to Asians), such as a yellowish black color series.

In one embodiment of the invention, the natural dye substance displaying the yellow or yellowish brown color series is selected from the group consisting of the quercetin or the derivative thereof, the extract containing the quercetin or the derivative thereof, and the mixture thereof, and displays the yellow or yellowish brown color series by itself or after forming complex with a metal salt; the quercetin derivative is such as rutin, polystachoside, neoisorutin, guaijaverin or quercitroside; and the extract containing the quercetin or the derivative thereof is a plant extract in which the quercetin is the main component, such as a sophora japonica flower extract or a sophora japonica flower-bud extract.

The uses according to the third aspect of the invention, at least one of the natural dye substances display a color series rather than the yellow or yellowish brown color series, such as purple or purple-black color series, or blue or blue-black color series; preferably, the natural dye substance displaying the color series rather than the yellow or yellowish brown color series is selected from the group consisting of plant polyphenols and other natural dye substances; preferably, the plant polyphenols are such as gallic acid, hematoxylin, tea polyphenols, apple polyphenols, gallnut extract, pomegranate rind extract, gingko leaf extract or giant knotweed extract; preferably, the other natural dyes are such as indigo, gardenia blue, cocoa pigment, purple sweet potato pigment, purple cabbage pigment and algae blue pigment; or the natural dye substance displaying the color series rather than the yellow or yellowish brown color serie is a mixture of the plant polyphenols and other natural dyes; and the natural substance itself or after forming a complex with a metal salt displays the purple or purple-black color series, or the blue or blue-black color series.

In one embodiment of the invention, by compounding the natural dye substance displaying the yellow or yellowish brown color series with the natural dye substance displaying the purple or purple-black color series, the color series which is close to the natural hair color of human (in particular to Asians), such as the yellowish black color series, can be obtained by color superposition.

The uses according to the third aspect of the invention, the content of the natural dye substances accounts for 0.05-20% of the total weight of the hair dye product, preferably 0.5-15%, and more preferably 1-10%.

In the invention, the proportion between the natural dye substances forming different color series is not particularly limited, and those skilled in the art can adjust the proportion according to practical needs. For example, if people would like to have darker hair colors, the amount of the natural dye substance displaying the blue-black or purple-black color series should be increased; and if people would like to have the yellower hair colors, the amount of the natural dye substance displaying the yellow or yellowish brown color series should be increased.

In one embodiment of the invention, the content of the natural dye substance displaying the yellow or yellowish brown color series accounts for 0.02-2% of the total weight of the hair dye product, such as 0.05-1.5%, and such as 0.1-0.6%; and the content of the natural dye substance displaying the blue-black or purple-black color series accounts for 0.01-15% of the total weight of the hair dyeing product, such as 0.5-12%, and such as 1-7%.

The uses according to the third aspect of the invention, the product for human or animal hair dyeing further comprises a metal salt. When the natural dye substance is a plant polyphenol, it forms the complex with the metal salt. Therefore, when the natural dye substance is a plant polyphenol, the yellow or yellowish brown color series, the purple or purple-black color series, or the blue or blue-black color series refers to the color displayed by the plant polyphenol itself or after forming the complex with the metal salt.

In the invention, the metal salt is divalent. In one embodiment of the invention, the metal salt is a ferrous salt. The ferrous salt is selected from one of ferrous sulfate, ferrous nitrate, ferrous gluconate, ferrous lactate, ferrous fumarate and etc., or is a mixture of any two or more of the above substances.

In the invention, the content of the metal salt accounts for 0.05-20% of the total weight of the hair dye product, preferably 0.5-15%, and more preferably 1%-12%.

The product provided by the invention has good safety, and the operations of softening the hair and dyeing the hair can be performed at the same time. According to the difference of the preparation, the softening preparation, the dye preparation and the mordant preparation can be respectively packaged and stored during storage, and when in use, the three preparations can be combined together and smeared on the hair, or respectively smeared on the hair, and then the white hair can be dyed into black or other colors.

Thus, the invention also relates to a method of using the product or the combined product for human or animal hair dyeing, which is selected from one of the following methods:

(1) The different preparations of each formulation of the combined product of the invention are separately smeared on hair and stay for a period of time between each preparation smearing;

(2) Some of the preparations of each formulation of the combined product of the invention are mixed and smeared on the hair, then the other preparations are separately smeared on the hair, and stay for a period of time between each preparation smearing; and (3) All the preparations of each formulation of the combined product of the invention are mixed, then smeared on the hair and stay for a period of time.

The using method according to the fourth aspect of the invention, the staying time does not need to be strictly limited, for example, the staying time can be more than 5 min, more than 10 min or more than 20 min. In the embodiment of the invention, for example, the staying time can be 5-10 mins, or 20-30 mins.

Unless expressly defined in this description, the scientific terms in the invention have the meanings which are well known in the art or are commonly understood by those skilled in the art.

The "effective amount" in the invention refers to the amount required for realizing the function of the corresponding component.

In the invention, the natural dye substances refer to dyes which are obtained from plants, animals or mineral resources, not synthesized artificially and subject to little or no chemical processing.

In the invention, the plant polyphenol is also known as vegetable tannin, which is secondary metabolite of complex phenols in plants, has polyphenol structures and mainly exists in peels, roots, leaves and fruits of the plants; and according to the structures, the numbers of phenol rings and the different functions of combining elements for combing with other rings, the plant polyphenol can be divided into phenolic acids, flavonoids, 1,2-stilbene compounds, lignans and the like.

In the invention, the plant polyphenol is selected from one of the phenolic acids (such as tea polyphenols, gallic acid, gallic tannins, tannic acid tannins, apple polyphenols and the like), the flavonoids (such as quercetin, rutin and the like), the 1,2-stilbene compounds (such as resveratrol and the like), the hematoxylin and the like, or a mixture of optionally two or more types of the above substances. The tannic acid tannin for example comprises tannic acid, tannic acid, giant knotweed tannic acid and the like.

The plant polyphenols can be complexed with the metal salt to form the colored complex, for example, the gallic acid is complexed with the metal salt to form the purple or purple-black complex, and the quercetin is complexed with the metal salt to form the yellow or yellowish brown complex.

In one embodiment of the invention, the natural dye substance is gallic acid and quercetin, respectively, or gallic acid, quercetin and rutin.

In another embodiment of the invention, the natural dye substance is tea polyphenols and quercetin, respectively, or tea polyphenols, quercetin and rutin.

In another embodiment of the invention, the natural dye substance is tea polyphenols, gallic acid and rutin, respectively.

In another embodiment of the invention, the natural dye substance is hematoxylin and quercetin, respectively, or hematoxylin, quercetin and rutin, respectively.

In another embodiment of the invention, the natural dye substance is quercetin and apple polyphenols, respectively.

In another embodiment of the invention, the natural dye substance is gallic acid, logwood extract and rutin, respectively.

In another embodiment of the invention, the natural dye substance is gallic acid, tea polyphenols and rutin, respectively.

In another embodiment of the invention, the natural dye substance is tea polyphenols, quercetin and sophora japonica flower-bud extract, respectively.

In another embodiment of the invention, the natural dye substance is pomegranate rind extract (or gallnut extract) and quercetin, respectively.

In another embodiment of the invention, the natural dye substance is tea polyphenols and sophora japonica flower extract, respectively.

In another embodiment of the invention, the natural dye substance is tea polyphenols, gingko leaf extract and quercetin, respectively.

In another embodiment of the invention, the natural dye substance is gallic acid, quercetin and gallnut extract, respectively.

In another embodiment of the invention, the natural dye substance is giant knotweed extract and quercetin, respectively.

In another embodiment of the invention, the natural dye substance is quercetin and indigo, respectively.

The plant polyphenols of the invention can be derived from natural plants, and can be extracts or monomers; and can be prepared by methods known in the prior art, such as a solvent extraction method, a supercritical fluid extraction method, an ultrasonic extraction method, a microwave extraction method and the like, and can also be obtained with synthesis methods.

In the invention, the dyeing component and the color-matching component are not strictly defined, the color-matching component is selected from one of the natural dye substances of the invention or the mixture of optionally two or more of the natural dye substances, and the color-matching component is different from the dyeing component and displays different color series from the dyeing component. Namely, in the invention, when one or more of the natural dye substances are called as the color-matching component, the other natural dye substances can be called as the dyeing component.

In the invention, the color series refers to a series of similar colors.

In the invention, the purple or purple-black color series comprises purple, dark purple, deep purple, purple-black and other similar colors; the blue or blue-black color series comprises blue, deep blue, indigo, purplish blue, navy blue, blue-black, dark blue and other similar colors; and the yellow or yellowish brown color series comprises yellow, brown, yellowish brown, reddish brown, brown, tan, iron brown and other similar colors.

In the invention, the color displayed after hair dyeing refers to the color displayed after dyeing of the white hair. In an embodiment of the invention, the white hair displays yellowish black color after dyeing, and displays yellowish black (sepia and black brown) color particularly under sunlight irradiation. The color is very close to the natural hair color of the yellow race, and the color is natural. However, by using the natural hair dye products in the prior art, the dyed hair usually displays the purplish black color under the sunlight irradiation, which is quite different from the natural hair color of people, and the color is also unnatural.

According to the invention, the product for human or animal hair dyeing can be the single-formulation product with the function of dyeing, or a combined product which comprises the softening preparation, the dye preparation and the mordant preparation or a combined product of preparations having the equivalent effect, as well as a product which is a part of the hair dye product and has the dyeing effect.

The combined product according to the invention, the mordant preparation further comprises an antioxidant. The antioxidant includes, but is not limited to one or more of ascorbic acid or salts thereof, cysteine or the derivative and the salts thereof (such as ascorbic acid, sodium ascorbate, cysteine, cysteine hydrochloride, N-acetylcysteine and reduced glutathione) and urea. In one embodiment of the invention, the disulfide bond reducing agent is selected from acetylcysteine or the salts thereof, cysteine or a hydrochloride thereof and reduced glutathione. In one embodiment of the invention, the antioxidant is selected from cysteine or the derivative and the salts thereof. In one embodiment of the invention, the antioxidant is selected from D-cysteine, L-cysteine, DL-cysteine, N-acetylcysteine and the salts thereof. In one embodiment of the invention, the antioxidant is selected from cysteine hydrochloride. In the combined product according to the aspect, the antioxidant is one antioxidant or any combination of a variety of antioxidants. In the combined product according to the aspect, the antioxidant accounts for 0.1-2% (by weight) of the total weight of the mordant preparation. In one embodiment of the invention, the antioxidant accounts for 0.2-1% (by weight) of the total weight of the mordant preparation.

The combined product according to the invention, the dye preparation and/or the mordant preparation further comprises a penetration enhancer (namely, a penetration accelerator) and a thickener (namely, a viscosity modifier for regulating the state of fluid (such as, liquid, semi-solid and the like)), as well as an optionally preservative.

The combined product according to the invention, the penetration enhancer in the mordant preparation includes, but is not limited to, chemical penetration enhancer: azone and homologs thereof, organic acids and esters thereof, organic solvents, surfactants, such as anion surfactants, non-ionic surfactants and amphoteric surfactants and the like; traditional Chinese medicine penetration enhancer: comprising terpenes, essential oils, lactones and the like; and any combination of the above substances. In one embodiment of the invention, the penetration enhancer is selected from one of the following substances: oleyl alcohols (such as cetyl/stearyl alcohol), dodecyl sulfates, dodecyl sulfonates and other anion surfactants, fatty alcohol ethers (such as cetyl stearyl ether) and other non-ionic surfactants, cocoylpropylbetaine and other amphoteric surfactants, or any combination thereof. In one embodiment of the invention, the penetration enhancer can be selected from one of oleyl alcohols, dodecyl sulfates and other anion surfactants, fatty alcohol ethers and other non-ionic surfactants, cocoylpropylbetaine and other amphoteric surfactants, or any combination thereof. According to the invention, the penetration enhancer can be one or any combination of a variety of penetration enhancer. In one embodiment of the invention, the penetration enhancer accounts for 1-10% (by weight) of the total weight of the mordant preparation. In one embodiment of the invention, the penetration enhancer accounts for 2-8% (by weight) of the total weight of the mordant preparation.

The combined product according to the invention, the thickener in the mordant preparation includes but is not limited to one or more of fatty alcohols or carbomers, hydroxyethyl cellulose, hydroxypropylmethyl cellulose and other high polymers. The weight percentage of the thickener in the mordant preparation can be determined by those skilled in the art according to the teachings of the invention in combination with the prior art. In one embodiment of the invention, the thickener accounts for 1-10% (by weight) of the total weight of the mordant preparation. In an embodiment of the invention, the thickener accounts for 2-8% (by weight) of the total weight of the mordant preparation.

The combined product according to the invention, further comprises a preservative. The preservative in the mordant preparation includes, but is not limited to, parabens, such as methyl paraben, ethyl paraben, propyl paraben and butyl paraben. The preservative can be one or any combination of a variety of preservatives, such as a combination of methyl paraben and propyl paraben in any proportion. The weight percentage of the preservative in the mordant preparation can be determined by those skilled in the art according to the teachings of the invention in combination with the prior art. In one embodiment of the invention, the preservative accounts for 0.1-0.8% (by weight) of the total weight of the mordant preparation. In one embodiment of the invention, the preservative accounts for 0.2-0.6% (by weight) of the total weight of the mordant preparation.

The combined product according to the invention, the mordant preparation is milky, pasty or gelatinous.

The combined product according to the invention, the penetration enhancer in the dye preparation includes, but is not limited to, chemical penetration enhancers, which comprises azone and homologs thereof, organic acids and esters thereof, organic solvents, surfactants, such as anion surfactants, non-ionic surfactants and amphoteric surfactants and the like; traditional Chinese medicine penetration enhancers, which comprises terpenes, essential oils, lactones and the like; and any combination of the above substances. In one embodiment of the invention, the penetration enhancer can be selected from one of the following substances: oleyl alcohols (such as cetyl/stearyl alcohol), dodecyl sulfates (such as sodium dodecyl sulfate), dodecyl sulfonates and other anion surfactants, fatty alcohol ethers (such as cetyl stearyl ether) and other non-ionic surfactants, cocoylpropylbetaine and other amphoteric surfactants, or any combination thereof. In one embodiment of the invention, the penetration enhancer can be selected from one of oleyl alcohols, dodecyl sulfates and other anion surfactants, fatty alcohol ethers and other non-ionic surfactants, cocoylpropylbetaine and other amphoteric surfactants, or any combination thereof. According to the invention, the penetration enhancer can be one penetration enhancer or any combination of a variety of penetration enhancer. In one embodiment of the invention, the penetration enhancer accounts for 2-15% (by weight) of the total weight of the dye preparation. In one embodiment of the invention, the penetration enhancer accounts for 3-10% (by weight) of the total weight of the dye preparation.

The combined product according to the invention, the thickener in the dye preparation includes, but is not limited to, one or more of fatty alcohols or carbomers, hydroxyethyl cellulose, hydroxypropylmethyl cellulose and other high polymers. In one embodiment of the invention, the weight percentage of the thickeners in the dye preparation can be determined by those skilled in the art according to the teachings of the invention in combination with the prior art. In one embodiment of the invention, the thickener accounts for 1-10% (by weight) of the total weight of the dye preparation. In one embodiment of the invention, the thickener accounts for 2-8% (by weight) of the total weight of the dye preparation.

The combined product according to the invention, the preservative in the dye preparation includes, but is not limited to, parabens, such as methyl paraben, ethyl paraben, propyl paraben and butyl paraben. The preservatives can be one or any combination of a variety of preservatives, such as the combination of methyl paraben and propyl paraben in any proportion. The weight percentage of the preservative in the dye preparation can be determined by those skilled in the art according to the teachings of the invention in combination with the prior art. In one embodiment of the invention, the preservative accounts for 0.1-0.8% (by weight) of the total weight of the dye preparation. In one embodiment of the invention, the preservative accounts for 0.2-0.6% (by weight) of the total weight of the dye preparation.

The combined product according to the invention, the dye preparation is milky, pasty or gelatinous.

The combined product according to the invention, the hair softening preparation can comprise one or more of disulfide bond reducing agent, alkalizer, penetration enhancer and thickener.

Wherein, the disulfide bond reducing agent includes, but is not limited to, one or more of acetylcysteine or derivatives and salts thereof, urea, thiosulfates (such as sodium thiosulfate), sulfites (such as sodium sulfite) and bisulfates. In one embodiment of the invention, the disulfide bond reducing agent is selected from acetylcysteine or the salts thereof, cysteine or a hydrochloride thereof, reduced glutathione, sulfite and bisulfite. In one embodiment of the invention, the disulfide bond reducing agent accounts for 2-25% (by weight) of the total weight of the softening preparation. In one embodiment of the invention, the disulfide bond reducing agent accounts for 4-15% (by weight) of the total weight of the softening preparation.

Wherein, the alkalizer is selected from one or more of the following alkalizer: ornithine, arginine, lysine, ammonia, ethanolamines (such as, monoethanolamine, diethanolamine or triethanolamine), alkyl alcohol amide, hydroxides or carbonate-containing compositions. In one embodiment of the invention, the alkalizer in the softening preparation accounts for 0.5-20% (by weight) of the total weight of the softening preparation. In one embodiment of the invention, the alkalizer in the softening preparation accounts for 2-18% (by weight) of the total weight of the softening preparation. The final pH value of the hair softening preparation is 9.0-10.0, for example 9.2-9.8; and in one embodiment of the invention, the final pH value of the hair softening preparation is 9.5.

Wherein, the softening preparation further comprises a penetration enhancer (namely a penetration accelerator). The penetration enhancer in the softening preparation includes, but is not limited to, chemical penetration enhancer, which comprises azone and homologs thereof, organic acids and esters thereof, organic solvents, surfactants, such as anion surfactants, non-ionic surfactants and amphoteric surfactants and the like; traditional Chinese medicine permeation enhancer, which comprises terpenes, essential oils, lactones and the like; and any combination of the above substances. In one embodiment of the invention, the penetration enhancer in the softening preparation can be selected from one of the following substances: oleyl alcohols, dodecyl sulfates (such as sodium dodecyl sulfate), dodecyl sulfonates and other anion surfactants, fatty alcohol ethers and other non-ionic surfactants, cocoylpropylbetaine and other amphoteric surfactants, or any combination thereof. In one embodiment of the invention, the penetration enhancer in the softening preparation can be selected from one of oleyl alcohols, dodecyl sulfates and other anion surfactants, fatty alcohol ethers and other non-ionic surfactants, cocoylpropylbetaine and other amphoteric surfactants, or any combination thereof. According to the invention, the penetration enhancer in the softening preparation can be one penetration enhancer or any combination of a variety of penetration enhancers. For example, the penetration enhancer can be used and selected from one or more of the following components: sodium dodecyl sulfate, sodium lauryl ether sulfate and cocoylpropylbetaine. In one embodiment of the invention, the penetration enhancer in the softening preparation accounts for 1-10% (by weight) of the total weight of the softening preparation. In one embodiment of the invention, the penetration enhancer accounts for 2-8% (by weight) of the total weight of the softening preparation.

According to the invention, the softening preparation further comprises a thickener (namely a viscosity modifier for regulating the state of fluid (such as, liquid, semi-solid and the like)). The thickeners in the softening preparation include, but are not limited to, one or more of fatty alcohols or carbomers, hydroxyethyl cellulose, hydroxypropylmethyl cellulose, xanthan gum and other high polymers. The weight percentage of the thickener in the softening preparation can be determined by those skilled in the art according to the teachings of the invention in combination with the prior art. In one embodiment of the invention, the thickener in the softening preparation accounts for 0.1-2% (by weight) of the total weight of the softening preparation. In one embodiment of the invention, the thickener in the softening preparation accounts for 0.2-1% (by weight) of the total weight of the softening preparation.

According to the invention, the softening preparation is milky, pasty or gelatinous.

In an embodiment of the invention, in addition to the natural dye substance, the hair softening preparation comprises an effective amount for softening the hair of N-acetylcysteine, L-cysteine hydrochloride, sodium sulfite, sodium dodecyl sulfate, carbomer, disodium edetate and monoethanolamine; or cysteine, sodium sulfite, urea, L-cysteine hydrochloride, sodium dodecyl sulfate, carbomer, disodium edetate and monoethanolamine; or N-acetylcysteine, sodium sulfite, cocoylpropylbetaine, hydroxyethyl cellulose, L-cysteine hydrochloride, sodium dodecyl sulfate, disodium edetate and monoethanolamine; or N-acetylcysteine, sodium sulfite, xanthan gum, L-cysteine hydrochloride, sodium dodecyl sulfate, carbomer, disodium edetate and monoethanolamine; or N-acetylcysteine, L-cysteine hydrochloride, sodium dodecyl sulfate, hydroxypropylmethyl cellulose, disodium edetate and monoethanolamine; or N-acetylcysteine, xanthan gum, L-cysteine hydrochloride, sodium dodecyl sulfate, disodium edetate and monoethanolamine.

In an embodiment of the invention, in addition to the natural dye substance, the dye preparation comprises an effective amount of cetyl/stearyl alcohol, cetearyl alcohol ether-6, sodium dodecyl sulfate, lanolin, white Vaseline, sodium sulfite, disodium edetate, methyl paraben and propyl paraben.

In an embodiment of the invention, in addition to the natural dye substance, the mordant preparation comprises an effective amount of ferrous sulfate, cetyl/stearyl alcohol, cetearyl alcohol ether-6, methyl paraben, propyl paraben and cysteine hydrochloride; or ferrous sulfate, cetyl/stearyl alcohol, cetearyl alcohol ether-6, sodium dodecyl sulfate, lanolin, white Vaseline, L-cysteine hydrochloride, methyl paraben and propyl paraben.

In an embodiment of the invention, in addition to the natural dye substance, the hair dye preparation (comprising the dye preparation and the mordant preparation) comprises an effective amount of ferrous sulfate, cetyl/stearyl alcohol, cetearyl alcohol ether-6, sodium dodecyl sulfate, lanolin, white Vaseline, L-cysteine hydrochloride, methyl paraben and propyl paraben.

The dye preparation or the natural dye substance can be respectively or totally combined into the hair softening preparation or the mordant preparation.

Since natural dyes have larger molecules, the speed of getting into the hair is slower. The invention firstly utilizes the softening preparation (also known as softening treatment agent) to soften the hair, so that the dye molecules can easily get into the hair to shorten the hair dyeing time.

The dyeing component and the color-matching component play a color-developing effect and can display different color series after getting into the hair. After the two components are compounded, a new color is produced by color superposition, for example, after a tan color and a purple-black color get into the hair for superposition, a black brown color is produced, and the color is natural.

For the dye preparation (also known as dye agent), the plant polyphenols, which can be used as the dyeing component and the color-matching component, is taken as the main active ingredient, and conventional substances are added, particularly those used in skin external productions and applicable for contacting skin, (such as the substances which do not produce irritation and other side effects against the skin), in particular antioxidant, penetration enhancer, thickener and the like which can be used in cosmetics, thereby resulting in forming any formulation suitable for hair dyeing, such as a solution, emulsion, paste, cream or gel form.

In the invention, for the mordant preparation (also known as mordant agent or metal ion agent), when the natural dye substances are plant polyphenols, metal ions in the natural dye substances are chelated with dye active substances to form larger molecules, thereby changing the colors displayed by the dyes, enabling the molecules to be larger and be less prone to getting out of the hair after hair dyeing, and further achieving the purpose of permanent hair dyeing. When the metal salt is a ferrous salt, the mordant preparation takes a compound containing ferrous ions as a main active component, and when hair dyeing is performed, the ferrous ions are oxidized into iron ions with the help of air then reacted with the plant polyphenols to form a colored complex. The conventional substances can be added, particularly those used in skin external productions and applicable for contacting skin (such as the substances which do not produce irritation and other side effects against the skin), in particular thinner, surfactant, thickener and the like which can be used in cosmetics, thereby resulting in forming any formulation which is suitable for hair dyeing, such as a solution, emulsion, paste, cream or gel form.

Beneficial Effects of the Invention

Compared with the existing products, the hair dyes taking the plant polyphenols as the dyestuff has the following advantages:

1) The hair dyes is safe, non-toxic and non-irritating and has no side effects and no allergies.

2) The operation is simple and convenient, the dyeing speed is fast and the dyeing time is short.

3) The fastness is good, the color is less prone to fading and can be resistant to washing by using commercially available shampoo for more than 50 times after dyeing.

4) The color after compounding is natural and similar to natural color hair, and remains no hair dyeing traces.

Specific Mode for Carrying out the Invention

The embodiments of the invention are described in detail by combining the following examples, comparative examples and test examples. However, a person skilled in the art would understand that the following examples are only used to illustrate the invention rather than defining the scope of the invention. When no particular conditions are specified in the examples, the examples are carried out under conventional conditions or the conditions recommended by the manufacturer. The agents or instruments, whose manufacturers are not indicated, are conventional products that are available commercially.

EXAMPLE 1

1) A softening preparation (prepared according to a total weight of 100 g): 6 g of N-acetylcysteine, 0.1 g of L-cysteine hydrochloride, 4 g of sodium dodecyl sulfate, 0.5 g of carbomer and 0.2 g of disodium edetate are fully uniformly mixed, then an appropriate amount of monoethanolamine is added to adjust the pH value so that the final pH value of the product reaches 9.5 (by a test paper), the balance of deionized water is added till 100 g, mixed and stirred evenly to afford a gel.

2) A dye preparation (a dyeing component or a color-matching component) (prepared according to a total weight of 100 g): 4 g of gallic acid (purchased from Sinopharm Chemical Reagent Co., Ltd., Batch No.: F20100427), 5 g of cetyl/stearyl alcohol, 5 g of cetearyl alcohol ether-6, 2 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, mixed and stirred evenly to afford a paste.

3) The dye preparation (the dyeing component or the color-matching component) (prepared according to a total weight of 100 g): 1 g of quercetin (purchased from Sinopharm Chemical Reagent Co., Ltd., Batch No.: F20101213), 5 g of cetyl/stearyl alcohol, 5 g of cetearyl alcohol ether-6, 2 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, mixed and stirred evenly to afford the paste.

4) A mordant preparation (prepared according to a total weight of 100 g): 5 g of ferrous sulfate, 5 g of cetyl/stearyl alcohol, 5 g of cetearyl alcohol ether-6, 0.25 g of methyl paraben, 0.15 g of propyl paraben and 0.5 g of cysteine hydrochloride are fully uniformly mixed, then the balance of deionized water is added, and mixed and stirred evenly to afford the paste.

5) A hair dyeing experiment of a hair tress: when in use, equal volumes of the first preparation, the second preparation, the third preparation and the fourth preparation are added into a non-metal container, uniformly stirred with a non-metal rod, hair washing is not required, the mixed hair dye is repeatedly uniformly smeared on the hair by using a hair comb and stay for 20-30 mins, then the hair is rinsed with warm water and air-dried or blow-dried.

The results show that the hair tress dyed by using the hair dye product of the embodiment has good color fastness and natural color.

EXAMPLE 2

1) A softening preparation (prepared according to a total weight of 100 g): 1.5 g of cysteine, 2.0 g of sodium sulfite, 0.5 g of urea, 0.1 g of L-cysteine hydrochloride, 4 g of sodium dodecyl sulfate, 0.5 g of carbomer and 0.2 g of disodium edetate are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to afford a gel.

2) A dye preparation (a dyeing component and a color-matching component) (prepared according to a total weight of 100 g): 0.05 g of hematoxylin (purchased from Shanghai Qcbio Science & Technologies Co., Ltd.), 0.1 g of quercetin (purchased from Sinopharm Chemical Reagent Co., Ltd., Batch No.: F20101213), 5 g of cetyl/stearyl alcohol, 5 g of cetearyl alcohol ether-6, 1 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, and mixed and uniformly stirred to afford a paste.

3) A mordant preparation (prepared according to a total weight of 100 g): 5 g of ferrous sulfate, 5 g of cetyl/stearyl alcohol, 5 g of cetearyl alcohol ether-6, 0.25 g of methyl paraben, 0.15 g of propyl paraben and 0.5 g of cysteine hydrochloride are fully uniformly mixed, then the balance of deionized water is added, and mixed and uniformly stirred to afford a paste.

4) A hair dyeing experiment of a hair tress: when in use, equal volumes of the first preparation and the second preparation are added into a non-metal container, uniformly stirred with a non-metal rod, hair washing is not required, the mixed hair dye is repeatedly uniformly smeared on the hair by using a hair comb and stay for 20-30 mins, hair washing is not required, the third preparation is uniformly smeared on the hair and stay for 5-10 mins, then the hair is rinsed with warm water and air-dried or blow-dried.

The results show that the hair tress dyed by using the hair dye product of the embodiment has good color fastness and natural color.

EXAMPLE 3

1) A softening preparation (prepared according to a total weight of 100 g): 15 g of N-acetylcysteine, 0.1 g of L-cysteine hydrochloride, 4 g of sodium dodecyl sulfate, 1 g of carbomer, 0.2 g of disodium edetate and 0.2 g of rutin (purchased from Sinopharm Chemical Reagent Co., Ltd., Batch No.: U1606503) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to obtain a gel.

2) A dye preparation (a dyeing component or a color-matching component) (prepared according to a total weight of 100 g): 2 g of gallic acid (purchased from Sinopharm Chemical Reagent Co., Ltd., Batch No.: F10100427), 5 g of logwood extract (the active component is hematoxylin, purchased from Daxing'anling Koralle Bioengineering Co., Ltd.), 1 g of cetyl/stearyl alcohol, 10 g of cetearyl alcohol ether-6, 4 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, and mixed and uniformly stirred to obtain a paste.

3) A mordant preparation (prepared according to a total weight of 100 g): 10 g of ferrous sulfate, 8 g of cetyl/stearyl alcohol, 3 g of cetearyl alcohol ether-6, 0.25 g of methyl paraben, 0.15 g of propyl paraben and 1 g of cysteine hydrochloride are fully uniformly mixed, then the balance of deionized water is added, and mixed and uniformly stirred to obtain the paste.

4) A hair dyeing experiment of a hair tress: when in use, equal volumes of the first preparation, the second preparation and the third preparation are added into a non-metal container, uniformly stirred with a non-metal rod, hair washing is not required, the mixed hair dye is repeatedly uniformly smeared on the hair by using a hair comb and stayed for 20-30 mins and then the hair is rinsed with warm water and air-dried or blow-dried.

The results show that the hair tress dyed by using the hair dye product of the embodiment has good color fastness and natural color.

EXAMPLE 4

1) A softening preparation (prepared according to a total weight of 100 g): 10 g of N-acetylcysteine, 1 g of sodium sulfite, 2 g of cocoylpropylbetaine, 1 g of hydroxyethyl cellulose, 0.1 g of L-cysteine hydrochloride, 4 g of sodium dodecyl sulfate and 0.2 g of disodium edetate are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A hair dyeing preparation (prepared according to a total weight of 100 g): 5 g of ferrous sulfate, 0.5 g of quercetin (purchased from Sinopharm Chemical Reagent Co., Ltd., Batch No.: F20101213), 4 g of tea polyphenols (purchased from Zhejiang Painuo Biotechnology Co., Ltd.), 5 g of cetyl/stearyl alcohol, 5 g of cetearyl alcohol ether-6, 2 g of sodium dodecyl sulfate, 2 g of lanolin, 2 g of white Vaseline, 0.5 g of L-cysteine hydrochloride, 0.25 g of methyl paraben and 0.15 g of propyl paraben are fully uniformly mixed, then the balance of deionized water is added, and mixed and uniformly stirred to get a paste.

3) A hair dyeing experiment of a hair tress: when in use, equal volumes of the first preparation and the second preparation are added into a non-metal container, uniformly stirred with a non-metal rod, hair washing is not required, the mixed hair dye after is repeatedly uniformly smeared on the hair by using a hair comb and stay for 20-30 mins, then the hair is rinsed with warm water and air-dried or blow-dried.

The results show that the hair tress dyed by using the hair dye product of the embodiment has good color fastness and natural color.

EXAMPLE 5

1) A softening preparation (prepared according to a total weight of 100 g): 4 g of N-acetylcysteine, 1 g of sodium sulfite, 2 g of xanthan gum, 0.1 g of L-cysteine hydrochloride, 4 g of sodium dodecyl sulfate, 0.5 g of carbomer, 0.2 g of disodium edetate and 2 g of rutin (purchased from Sinopharm Chemical Reagent Co., Ltd., Batch No.: U1606503) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A hair dyeing preparation (prepared according to a total weight of 100 g): 5 g of ferrous sulfate, 10 g of gallic acid (purchased from Sinopharm Chemical Reagent Co., Ltd., Batch No.: F20100427), 10 g of tea polyphenols (purchased from Zhejiang Painuo Biotechnology Co., Ltd.), 5 g of cetyl/stearyl alcohol, 5 g of cetearyl alcohol ether-6, 2 g of sodium dodecyl sulfate, 2 g of lanolin, 2 g of white Vaseline, 0.5 g of L-cysteine hydrochloride, 0.25 g of methyl paraben and 0.15 g of propyl paraben are fully uniformly mixed, then the balance of deionized water is added, and mixed and uniformly stirred to get a paste.

3) A hair dyeing experiment of a hair tress: when in use, equal volumes of the first preparation and the second preparation are added into a non-metal container, uniformly stirred with a non-metal rod, hair washing is not required, the mixed hair dye is repeatedly uniformly smeared on the hair by using a hair comb and stay for 20-30 mins and then the hair is rinsed with warm water and air-dried or blow-dried.

The results show that the hair tress dyed by using the hair dye product of the embodiment has good color fastness and natural color.

EXAMPLE 6

1) A softening preparation (prepared according to a total weight of 100 g): 6 g of N-acetylcysteine, 0.1 g of L-cysteine hydrochloride, 4 g of sodium dodecyl sulfate, 0.2 g of hydroxypropylmethyl cellulose, 0.2 g of disodium edetate, 0.2 g of quercetin (purchased from Sinopharm Chemical Reagent Co., Ltd., Batch No.: F20101213) and 4 g of tea polyphenols (purchased from Zhejiang Painuo Biotechnology Co., Ltd.) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A mordant preparation (prepared according to a total weight of 100 g): 5 g of ferrous sulfate, 5 g of cetyl/stearyl alcohol, 5 g of cetearyl alcohol ether-6, 2 g of sodium dodecyl sulfate, 2 g of lanolin, 2 g of white Vaseline, 0.5 g of L-cysteine hydrochloride, 0.25 g of methyl paraben and 0.15 g of propyl paraben are fully uniformly mixed, then the balance of deionized water is added, and mixed and uniformly stirred to get a paste.

3) A hair dyeing experiment of a hair tress: when in use, hair washing is not required, the first preparation is repeatedly uniformly smeared on the hair by using a hair comb and stay for 20-30 mins, the hair washing is not required, then the second preparation is uniformly smeared on the hair, and the hair is rinsed with warm water and air-dried or blow-dried.

The results show that the hair tress dyed by using the hair dye product of the embodiment has good color fastness and natural color.

EXAMPLE 7

1) A softening preparation (prepared according to a total weight of 100 g): 15 g of N-acetylcysteine, 2 g of xanthan gum, 0.1 g of L-cysteine hydrochloride, 4 g of sodium dodecyl sulfate, 0.2 g of disodium edetate and 0.5 g of quercetin (purchased from Sinopharm Chemical Reagent Co., Ltd., Batch No.: F20101213) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to obtain a gel.

2) A hair dyeing preparation (prepared according to a total weight of 100 g): 10 g of ferrous sulfate, 2 g of gallic acid (purchased from Sinopharm Chemical Reagent Co., Ltd., Batch No.: F20100427), 10 g of cetyl/stearyl alcohol, 1 g of cetearyl alcohol ether-6, 2 g of sodium dodecyl sulfate, 2 g of lanolin, 2 g of white Vaseline, 1 g of L-cysteine hydrochloride, 0.25 g of methyl paraben and 0.15 g of propyl paraben are fully uniformly mixed, then the balance of deionized water is added, and mixed and uniformly stirred to obtain a paste.

3) A hair dyeing experiment of a hair tress: when in use, hair washing is not required, the first preparation is repeatedly uniformly smeared on the hair by using a hair comb and stay for 20-30 mins, the hair washing is not required, then the second preparation is uniformly smeared on the hair and stay for 5-10 min, and the hair is rinsed with warm water and air-dried or blow-dried.

The results show that the hair tress dyed by using the hair dye product of the embodiment has good color fastness and natural color.

EXAMPLE 8

1) A softening preparation (prepared according to a total weight of 100 g): 6 g of N-acetylcysteine, 0.1 g of L-cysteine hydrochloride, 4 g of sodium dodecyl sulfate, 2 g of cocoylpropylbetaine, 0.5 g of hydroxyethyl cellulose, 0.5 g of carbomer, 0.2 g of disodium edetate, 0.2 g of quercetin (purchased from Sinopharm Chemical Reagent Co., Ltd., Batch No.: F20101213) and 0.2 g of sophora japonica flower-bud extract (quercetin is the main component, purchased from Xi'an KinGreen Bio-Engineering Technology Co., Ltd.) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A hair dyeing preparation (prepared according to a total weight of 100 g): 5 g of ferrous sulfate, 4 g of tea polyphenols (purchased from Zhejiang Painuo Biotechnology Co., Ltd.), 5 g of cetyl/stearyl alcohol, 5 g of cetearyl alcohol ether-6, 2 g of sodium dodecyl sulfate, 2 g of lanolin, 2 g of white Vaseline, 0.5 g of L-cysteine hydrochloride, 0.25 g of methyl paraben and 0.15 g of propyl paraben are fully uniformly mixed, then the balance of deionized water is added, and mixed and uniformly stirred to get a paste.

3) A hair dyeing experiment of a hair tress: when in use, hair washing is not required, the first preparation is repeatedly uniformly smeared on the hair by using a hair comb and stay for 20-30 mins, the hair washing is not required, then the second preparation is uniformly smeared on the hair and stay for 5-10 mins, and the hair is rinsed with warm water and air-dried or blow-dried.

The results show that the hair tress dyed by using the hair dye product of the embodiment has good color fastness and natural color.

EXAMPLE 9

1) A softening preparation (prepared according to a total weight of 100 g): 15 g of N-acetylcysteine, 0.1 g of L-cysteine hydrochloride, 4 g of sodium dodecyl sulfate, 0.5 g of carbomer, 0.2 g of disodium edetate and 1 g of quercetin (purchased from Sinopharm Chemical Reagent Co., Ltd., Batch No.: F20101213) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A dye preparation (a dyeing component or a color-matching component) (prepared according to a total weight of 100 g): 20 g of pomegranate rind extract (tannic acid is the main component, purchased from Xi'an Xiaocao Plant Technology Co., Ltd.), 5 g of cetyl/stearyl alcohol, 5 g of cetearyl alcohol ether-6, 2 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, and mixed and uniformly stirred to get a paste.

3) A mordant preparation (prepared according to a total weight of 100 g): 5 g of ferrous sulfate, 5 g of cetyl/stearyl alcohol, 5 g of cetearyl alcohol ether-6, 0.25 g of methyl paraben, 0.15 g of propyl paraben and 0.5 g of cysteine hydrochloride are fully uniformly mixed, then the balance of deionized water is added, and mixed and uniformly stirred to obtain a paste.

4) A hair dyeing experiment of a hair tress: when in use, equal volumes of the first preparation, the second preparation and the third preparation are added into a non-metal container, uniformly stirred with a non-metal rod, hair washing is not required, the mixed hair dye is repeatedly uniformly smeared on the hair by using a hair comb and stay for 20-30 mins, then the hair is rinsed with warm water and air-dried or blow-dried.

The results show that the hair tress dyed by using the hair dye product of the embodiment has good color fastness and natural color.

EXAMPLE 10

1) A softening preparation (prepared according to a total weight of 100 g): 1.5 g of cysteine, 0.5 g of sodium sulfite, 0.1 g of L-cysteine hydrochloride, 4 g of sodium dodecyl sulfate, 0.5 g of carbomer, 0.2 g of disodium edetate and 1.0 g of sophora japonica flower extract (quercetin is the main component, purchased from Guangxi Wanfeng Pharmaceutical Co., Ltd.) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A hair dyeing preparation (prepared according to a total weight of 100 g): 5 g of ferrous sulfate, 4 g of tea polyphenols (purchased from Zhejiang Painuo Biotechnology Co., Ltd.), 5 g of cetyl/stearyl alcohol, 5 g of cetearyl alcohol ether-6, 2 g of sodium dodecyl sulfate, 2 g of lanolin, 2 g of white Vaseline, 0.5 g of L-cysteine hydrochloride, 0.25 g of methyl paraben and 0.15 g of propyl paraben are fully uniformly mixed, then the balance of deionized water is added, and mixed and uniformly stirred to get a paste.

3) A hair dyeing experiment of a hair tress: when in use, hair washing is not required, the first preparation is repeatedly uniformly smeared on the hair by using a hair comb and stay for 20-30 mins, the hair washing is not required, then the second preparation is uniformly smeared on the hair and stay for 5-10 mins, and the hair is rinsed with warm water and air-dried or blow-dried.

The results show that the hair tress dyed by using the hair dye product of the embodiment has good color fastness and natural color.

EXAMPLE 11

1) A softening preparation (prepared according to a total weight of 100 g): 10 g of sodium thiosulfate, 0.5 g of L-cysteine hydrochloride, 4 g of sodium dodecyl sulfate, 0.5 g of carbomer, 0.2 g of disodium edetate and 1 g of quercetin (purchased from Sinopharm Chemical Reagent Co., Ltd., Batch No.: F20101213) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A dye preparation (a dyeing component or a color-matching component) (prepared according to a total weight of 100 g): 6 g of gallnut extract (tannic acid is the main component, purchased from Xi'an Xiaocao Plant Technology Co., Ltd.), 5 g of cetyl/stearyl alcohol, 5 g of cetearyl alcohol ether-6, 2 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, and mixed and uniformly stirred to obtain a paste.

3) A mordant preparation (prepared according to a total weight of 100 g): 5 g of ferrous sulfate, 5 g of cetyl/stearyl alcohol, 5 g of cetearyl alcohol ether-6, 0.25 g of methyl paraben, 0.15 g of propyl paraben and 0.5 g of cysteine hydrochloride are fully uniformly mixed, then the balance of deionized water is added, and mixed and uniformly stirred to obtain a paste.

4) A hair dyeing experiment of a hair tress: when in use, equal volumes of the first preparation and the second preparation are added into a non-metal container, uniformly stirred with a non-metal rod, hair washing is not required, the mixed hair dye is repeatedly uniformly smeared on the hair by using a hair comb and stay for 20-30 mins, the hair washing is not required, the third preparation is uniformly smeared on the hair and stay for 5-10 mins and then the hair is rinsed with warm water and air-dried or blow-dried.

The results show that the hair tress dyed by using the hair dye product of the embodiment has good color fastness and natural color.

EXAMPLE 12

1) A softening preparation (prepared according to a total weight of 100 g): 1.5 g of cysteine, 2.0 g of sodium sulfite, 0.5 g of urea, 0.1 g of L-cysteine hydrochloride, 4 g of sodium dodecyl sulfate, 0.5 g of carbomer, 0.2 g of disodium edetate and 1 g of quercetin (purchased from Sinopharm Chemical Reagent Co., Ltd., Batch No.: F20101213) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to obtain a gel.

2) A dye preparation (a dyeing component or a color-matching component) (prepared according to a total weight of 100 g): 5 g of apple polyphenols (purchased from Hangzhou Skyherb Technologies Co., Ltd.), 5 g of cetyl/stearyl alcohol, 5 g of cetearyl alcohol ether-6, 2 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, and mixed and uniformly stirred to obtain a paste.

3) A mordant preparation (prepared according to a total weight of 100 g): 5 g of ferrous sulfate, 5 g of cetyl/stearyl alcohol, 5 g of cetearyl alcohol ether-6, 0.25 g of methyl paraben, 0.15 g of propyl paraben and 0.5 g of cysteine hydrochloride are fully uniformly mixed, then the balance of deionized water is added, and mixed and uniformly stirred to get a paste.

4) A hair dyeing experiment of a hair tress: when in use, equal volumes of the first preparation, the second preparation and the third preparation are added into a non-metal container, uniformly stirred with a non-metal rod, hair washing is not required, the mixed hair dye is repeatedly uniformly smeared on the hair by using a hair comb and stay for 20-30 mins and then the hair is rinsed with warm water and air-dried or blow-dried.

The results show that the hair tress dyed by using the hair dye product of the embodiment has good color fastness and natural color.

EXAMPLE 13

1) A softening preparation (prepared according to a total weight of 100 g): 15 g of N-acetylcysteine, 0.5 g of L-cysteine hydrochloride, 4 g of sodium dodecyl sulfate, 0.5 g of carbomer, 0.2 g of disodium edetate, 1 g of quercetin (purchased from Sinopharm Chemical Reagent Co., Ltd., Batch No.: F20101213) and 2 g of tea polyphenols (purchased from Zhejiang Painuo Biotechnology Co., Ltd.) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A dye preparation (a dyeing component or a color-matching component) (prepared according to a total weight of 100 g): 6 g of gingko leaf extract (tannic acid is the main component, purchased from Xi'an Xiaocao Plant Technology Co., Ltd.), 5 g of cetyl/stearyl alcohol, 5 g of cetearyl alcohol ether-6, 1 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, and mixed and uniformly stirred to get a paste.

3) A mordant preparation (prepared according to a total weight of 100 g): 5 g of ferrous sulfate, 5 g of cetyl/stearyl alcohol, 5 g of cetearyl alcohol ether-6, 0.25 g of methyl paraben, 0.15 g of propyl paraben and 0.5 g of cysteine hydrochloride are fully uniformly mixed, then the balance of deionized water is added, and mixed and uniformly stirred to obtain a paste.

4) A hair dyeing experiment of a hair tress: when in use, equal volumes of the first preparation and the second preparation are added into a non-metal container, uniformly stirred with a non-metal rod, hair washing is not required, the mixed hair dye is repeatedly uniformly smeared on the hair by using a hair comb and stay for 20-30 mins, the hair washing is not required, the third preparation is uniformly smeared on the hair and stay for 5-10 mins and then the hair is rinsed with warm water and air-dried or blow-dried.

The results show that the hair tress dyed by using the hair dye product of the embodiment has good color fastness and natural color.

EXAMPLE 14

1) A softening preparation (prepared according to a total weight of 100 g): 10 g of sodium thiosulfate, 5 g of sodium sulfite, 0.1 g of L-cysteine hydrochloride, 4 g of sodium dodecyl sulfate, 0.5 g of carbomer, 0.2 g of disodium edetate and 1 g of quercetin (purchased from Sinopharm Chemical Reagent Co., Ltd., Batch No.: F20101213) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to obtain a gel.

2) A dye preparation (a dyeing component and/or a color-matching component) (prepared according to a total weight of 100 g): 2 g of gallic acid (purchased from Sinopharm Chemical Reagent Co., Ltd., Batch No.: F20100427), 3 g of gallnut extract (tannic acid is the main component, purchased from Xi'an Xiaocao Plant Technology Co., Ltd.), 5 g of cetyl/stearyl alcohol, 5 g of cetearyl alcohol ether-6, 1 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, and mixed and uniformly stirred to get a paste.

3) A mordant preparation (prepared according to a total weight of 100 g): 5 g of ferrous sulfate, 5 g of cetyl/stearyl alcohol, 5 g of cetearyl alcohol ether-6, 0.25 g of methyl paraben, 0.15 g of propyl paraben and 0.5 g of cysteine hydrochloride are fully uniformly mixed, then the balance of deionized water is added, and mixed and uniformly stirred to get a paste.

4) A hair dyeing experiment of a hair tress: when in use, equal volumes of the first preparation and the second preparation are added into a non-metal container, uniformly stirred with a non-metal rod, hair washing is not required, the mixed hair dye is repeatedly uniformly smeared on the hair by using a hair comb and stay for 20-30 mins, the hair washing is not required, the third preparation is uniformly smeared on the hair and stay for 5-10 mins, then the hair is rinsed with warm water and air-dried or blow-dried.

The results show that the hair tress dyed by using the hair dye product of the embodiment has good color fastness and natural color.

EXAMPLE 15

1) A softening preparation (prepared according to a total weight of 100 g): 6 g of N-acetylcysteine, 0.1 g of L-cysteine hydrochloride, 4 g of sodium dodecyl sulfate, 0.5 g of carbomer and 0.2 g of disodium edetate are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A dye preparation (a dyeing component and a color-matching component) (prepared according to a total weight of 100 g): 6 g of giant knotweed extract (giant knotweed tannic acid is the main component, purchased from Xi'an Aojing Science and Technology Development Co., Ltd.), 1 g of quercetin (purchased from Sinopharm Chemical Reagent Co., Ltd., Batch No.: F20101213), 5 g of cetyl/stearyl alcohol, 5 g of cetearyl alcohol ether-6, 1 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, and mixed and uniformly stirred to get a paste.

3) A mordant preparation (prepared according to a total weight of 100 g): 5 g of ferrous sulfate, 5 g of cetyl/stearyl alcohol, 5 g of cetearyl alcohol ether-6, 0.25 g of methyl paraben, 0.15 g of propyl paraben and 0.5 g of cysteine hydrochloride are fully uniformly mixed, then the balance of deionized water is added, and mixed and uniformly stirred to get a paste.

4) A hair dyeing experiment of a hair tress: when in use, equal volumes of the first preparation and the second preparation are added into a non-metal container, uniformly stirred with a non-metal rod, hair washing is not required, the mixed hair dye is repeatedly uniformly smeared on the hair by using a hair comb and stay for 20-30 mins, the hair washing is not required, the third preparation is uniformly smeared on the hair and stay for 5-10 mins, and then the hair is rinsed with warm water and air-dried or blow-dried.

The results show that the hair tress dyed by using the hair dye product of the embodiment has good color fastness and natural color.

EXAMPLE 16

1) A softening preparation (prepared according to a total weight of 100 g): 15 g of N-acetylcysteine, 0.1 g of L-cysteine hydrochloride, 4 g of sodium dodecyl sulfate, 0.5 g of carbomer, 0.2 g of disodium edetate and 0.5 g of quercetin (purchased from Sinopharm Chemical Reagent Co., Ltd., Batch No.: F20101213) are fully uniformly mixed, then an appropriate amount of monoethanolamine is added to adjust the pH value so that the final pH value of the product reaches 9.5 (by a test paper), the balance of deionized water is added till 100 g, and mixed and uniformly stirred to get a gel.

2) A dye preparation (a dyeing component and a color-matching component) (prepared according to total weight of 100 g): 2 g of indigo (purchased from Sensient Technologies Corporation (China), Batch No.: 505960), 10 g of cetyl/stearyl alcohol, 3 g of cetearyl alcohol ether-6, 4 g of sodium dodecyl sulfate, 2 g of lanolin, 2 g of white Vaseline, 0.2 g of sodium sulfite, 0.2 g of disodium edetate, 0.25 g of methyl paraben and 0.15 g of propyl paraben are fully uniformly mixed, then the balance of deionized water is added, and mixed and uniformly stirred to get a paste.

3) A hair dyeing experiment of a hair tress: when in use, hair washing is not required, the first preparation is repeatedly uniformly smeared on the hair by using a hair comb and stay for 20-30 mins, the hair washing is not required, then the second preparation is uniformly smeared on the hair and stay for 5-10 mins, and the hair is rinsed with warm water and air-dried or blow-dried.

The results show that the hair tress dyed by using the hair dye product of the embodiment has good color fastness and natural color.

COMPARATIVE EXAMPLE 1

Hair Dyeing Agent Using Rutin or Quercetin as Dyestuff (CN1478459A)

1. According to the preparation method mentioned in the embodiment, the hair dye is a three-preparation product, including a first preparation, namely a softening treatment agent, a second preparation, namely a color developing agent and a third preparation, namely an ion chelating agent, and all of the three preparations are prepared into liquid.

2. A hair dyeing experiment of a hair tress: equal volumes of the first preparation and the second preparation are added into a non-metal container and fully uniformly stirred, a mixed solution is uniformly smeared on the hair by using a brush, then wait for 15-20 mins (the recommended temperature is 20-30° C.), then rinsed with water, the same operation is repeated with the third preparation, wait for 5 mins and then the hair is washed.

The results show that the hair tress dyed by the hair dye product of the comparative example is yellowish brown and the color is unnatural.

COMPARATIVE EXAMPLE 2

Gallic Acid Hair Dyes and Preparation Method and Uses Thereof (CN101869536A)

1. According to the preparation method mentioned in the embodiment, the hair dyes is a two-preparation product, including a dye preparation and a metallic ion chelating agent, and both of the preparations are prepared into liquid.

2. A hair dyeing experiment of a hair tress: the dye preparation is uniformly smeared on the hair, waiting for 20 mins, then the metal ion chelating agent is uniformly smeared on the hair, waiting for 20 mins, and then floating color on the hair is washed with shampoo.

The results show that the hair tress dyed by the hair dye product of the comparative example is deep purple black color and the color is unnatural.

COMPARATIVE EXAMPLE 3

Natural Hair Dyeing Agent Prepared by Plant Pigment Catechu and Hair Dyeing Method Thereof (CN101164528)

1. According to the preparation method mentioned in the embodiment, the hair dyes is a two-preparation product, including a dye preparation, named agent A, and a metallic ion chelating agent, named agent B, and both of the preparations are prepared into liquid.

2. A hair dyeing experiment of a hair tress: the agent A is firstly uniformly smeared on the hair, hair dyeing is performed for 40 mins at normal temperature, then the agent B is uniformly smeared on the hair, mordant dyeing is performed for 10 min and then the hair is washed and blow-dried.

The results show that the hair tress dyed by the hair dye product of the comparative example is deep purple black color and the color is unnatural.

COMPARATIVE EXAMPLE 4

A Hair Dyeing Agent Using Logwood Extract as Dyestuff (CN11561950)

1. According to the preparation method mentioned in the embodiment, the hair dye agent is a three-preparation product, including a first preparation, named a softening treatment agent, a second preparation, named a dye preparation and a third preparation, named an ion chelating agent, and all of the three preparations are prepared into liquid.

2. A hair dyeing experiment of a hair tress: equal volumes of the first preparation and the second preparation are added into a non-metallic container and fully uniformly stirred, a mixed solution is uniformly smeared on the hair by using a brush, waiting for 15-20 mins (the recommended temperature is 20-30° C.), then washed with water, the same operation is repeated with the third preparation, waiting for 5 min and then the hair is washed.

The results show that the hair tress dyed by the hair dye product of the comparative example is purple black color and the color is unnatural.

COMPARATIVE EXAMPLE 5

A Plant Hair Dye Agent (CN102198058A)

1. According to the preparation method mentioned in the embodiment, the hair dyeing agent is a two-preparation product, including a first preparation, named a softening treatment agent, and a second preparation, which is a hair dyeing preparation prepared by putting henna, tannic acid and ferrous salt together, and both of the preparations are prepared into liquid.

2. A hair dyeing experiment of a hair tress: after hair is cleaned and dried, the softening treatment agent is uniformly smeared on the hair and kept for 20 mins, then the hair is washed, then the hair dyeing agent is uniformly smeared on the hair and kept for 20 mins to 1.5 hours, and the hair is further washed.

The results show that the hair tress dyed by the hair dye product of the comparative example is brownish grey-black, and after the dyed hair is washed with commercially available shampoo for five times, the color fading is obvious.

Test Examples Tests of Color and Fastness of Hair Tress

1. Test Method:

Hair tress: grey hair taken from hair crown of one person with grey hair.

Standard hair samples: natural hair tresses (without dyeing) are taken from 20 healthy adults, Hunter parameters, namely L, a and b values are respectively determined and average values are respectively calculated.

Color of hair tress: the hair after dyeing is detected by a colorimeter and compared with the standard hair samples for Hunter parameters, namely L, a and b values, and naked-eye observation is simultaneously performed.

A Hunter-parameters method is a dyeing characterization method which is widely used in textile and dyeing industry in many foreign countries. The method has three main parameters, namely L, a and b. The parameters a and b can be positive or negative numbers, which are used for determining the color tone and are called as color indexes; the more positive the a value is, the redder the color is; the more negative the a value is, the greener the color is; and similarly, positive of b value represents yellow color, and negative of b value represents blue color. The parameter L is used for measuring the brightness of color, if L value is zero, the color is pure black, and if L value is 100, the color is pure white.

Fastness of hair tress: the hair after dyeing was irradiated under sunlight to examine the fastness to sunlight and the hair after dyeing is washed with commercially available shampoo to examine the fastness to washing.

2. Test Results:

Dyeing hair respectively according to the methods in the embodiments, the comparative example 1, the comparative example 2, the comparative example 3, the comparative example 4 and the comparative example 5, and compared the Hunter parameters, namely L, a and b values respectively with the standard hair samples, and the naked-eye observation is simultaneously performed.

The hair dyeing results of the hair tress using the hair dyeing agent of embodiment 1 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 2 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 3 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 4 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 5 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 6 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 7 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 8 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 9 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 10 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 11 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 12 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 13 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 14 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 15 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of embodiment 16 are as follows: the determination result of the colorimeter is black, the color is black according to the naked-eye observation, the color is yellowish black under light irradiation and the color is natural; and the fastness test results show that no color fading occurs after being irradiated under sunlight for 50 days and washed for 50 times.

The hair dyeing results of the hair tress using the hair dyeing agent of comparative example 1 are as follows: hair dyeing is performed at the temperature of 20° C. according to the using method mentioned in the embodiment, the coloring effect is far from ideal, the coloring effect at the temperature of 30° C. is slightly better, the determination result of the colorimeter is yellowish brown, the color is yellowish brown according to the naked-eye observation and the color is yellowish and blue-greenish yellow under light irradiation; and the test results of the fastness show that the color fading is obvious after being irradiated under sunlight for 50 days and washed for 50 times.

The hair dyeing results of the hair tress using the hair dyeing agent of comparative example 2 are as follows: the determination result of the colorimeter is deep purple black, the color is deep purple black according to the naked-eye observation, the color is purplish black under light irradiation and the color is unnatural; and the test results of the fastness show that no color fading occurs after being irradiated under sunlight for 50 days and washed for 50 times.

The hair dyeing results of the hair tress using the hair dye of comparative example 3 are as follows: the determination result of the colorimeter is deep purple black, the color is deep purple black according to the naked-eye observation, the color is purplish black under light irradiation and the color is unnatural; and the test results of the fastness show that no color fading occurs after being irradiated under sunlight for 50 days and washed for 50 times.

The hair dyeing results of the hair tress using the hair dye of comparative example 4 are as follows: the determination result of the colorimeter is purple black, the color is purple black according to the naked-eye observation, the color is purplish black under light irradiation and the color is unnatural; and the test results of the fastness show that no color fading occurs after being irradiated under sunlight for 50 days and washed for 50 times.

The hair dyeing results of the hair tress using the hair dye of comparative example 5 are as follows: the determination result of the colorimeter is black, the color is brownish grey-black, the color is yellowish and purplish black under light irradiation and the color is natural; and the test results of the fastness show that the color fading is obvious after being irradiated under sunlight for 50 days, the color is mauve, the color fading is obvious after being washed for 50 times, and the color is basically white.

The above test results show that, compared with the comparative examples 1, 2, 3, 4 and 5, the color of the hair which is dyed by using the products of the embodiments is natural and basically consistent with the real hair, the color can be kept for about 50 days without color fading and the hair dyeing effect is stable.

The differences in Hunter parameters, namely L, a and b values and the like between the dyed hair samples and the standard hair samples in 21 preparations (16 embodiments and 5 comparative examples) are listed in Table 1.

TABLE 1

| Test example | L | a | b | Naked-eye observation | Under Light irradiation |
|---|---|---|---|---|---|
| Standard hair sample | 15.51 | 1.35 | 1.04 | Black | Yellowish black |
| Embodiment 1 | 15.14 | 1.01 | 0.93 | Black | Yellowish black |
| Embodiment 2 | 14.98 | 0.82 | 1.20 | Black | Yellowish black |
| Embodiment 3 | 15.33 | 0.92 | 0.98 | Black | Yellowish black |
| Embodiment 4 | 15.16 | 1.24 | 1.15 | Black | Yellowish black |
| Embodiment 5 | 15.71 | 1.31 | 1.15 | Black | Yellowish black |
| Embodiment 6 | 15.86 | 0.95 | 0.91 | Black | Yellowish black |
| Embodiment 7 | 15.69 | 1.27 | 1.29 | Black | Yellowish black |
| Embodiment 8 | 15.84 | 0.85 | 1.14 | Black | Yellowish black |
| Embodiment 9 | 15.65 | 1.16 | 1.23 | Black | Yellowish black |
| Embodiment 10 | 15.37 | 1.22 | 1.05 | Black | Yellowish black |
| Embodiment 11 | 15.32 | 0.98 | 0.98 | Black | Yellowish black |
| Embodiment 12 | 15.77 | 0.89 | 1.01 | Black | Yellowish black |
| Embodiment 13 | 15.10 | 1.15 | 1.36 | Black | Yellowish black |
| Embodiment 14 | 15.56 | 1.07 | 1.25 | Black | Yellowish black |
| Embodiment 15 | 15.96 | 0.93 | 0.92 | Black | Yellowish black |
| Embodiment 16 | 15.44 | 0.95 | 1.17 | Black | Yellowish black |
| Comparative example 1 | 26.29 | 3.75 | 11.38 | Yellowish brown | Yellowish and blue-greenish grey |
| Comparative example 2 | 18.79 | 0.08 | −0.63 | Deep purple black | Purplish black |
| Comparative example 3 | 18.90 | 0.60 | −2.89 | Deep purple black | Purplish black |
| Comparative example 4 | 21.80 | 0.40 | −1.10 | Purple black | Purplish black |

TABLE 1-continued

| Test example | L | a | b | Naked-eye observation | Under Light irradiation |
|---|---|---|---|---|---|
| Comparative example 5 | 23.15 | 0.25 | 0.75 | Purple grey black | Yellowish and purplish black |

It can be seen from Table 1 that, the L values of the hair tresses dyed by the products of comparative examples 2, 3 and 4 are larger than the L value in the standard hair sample, indicating that the color is neither black enough nor bright enough; the b values are negative numbers, indicating that the color is blue, the color is purple according to the naked-eye observation and the color is very unnatural; and by comparing the hair tress dyed in the comparative example 1 with the standard hair sample, the L value is about 2 times of the standard hair sample, the color does not belong to the black scope, both of a and b values are larger than those in the standard hair sample and the color is redder and yellower than the standard hair sample; and the Hunter parameters, namely L, a and b values and the like of the hair samples dyed by the products of the embodiments are basically consistent with the standard hair sample and the color of hair is natural.

Although the embodiments of the invention are described in detail, a person skilled in the art would understand that various modification and substitutions may be made to these details on the basis of all the teachings disclosed. These changes fall into the protection scope of the invention. The scope of the invention is defined by the attached claims and an equivalent thereof.

The invention claimed is:

1. A product for human or animal hair dyeing, comprising:
effective amount of natural dye substances; and
optionally one or more excipients,
wherein the natural dye substance comprises at least two kinds of substances and displays at least two color series;
wherein a new color is produced by a superposition of the at least two color series;
wherein at least one of the at least two kinds of substances displays a yellow or yellowish brown color series;
wherein the at least one of the at least two kinds of substances displaying the yellow or yellowish brown color series is selected from the group consisting of quercetin or a derivative thereof, an extract containing quercetin or the derivative thereof, and a mixture thereof; and
wherein:
at least one of the at least two kinds of substances displays a color series other than the yellow or yellowish brown color series;
the color series other than the yellow or yellowish brown color series is a purple or purple-black color series, or a blue or blue-black color series;
the at least one of the at least two kinds of substances displaying the color series other than the yellow or yellowish brown color series is selected from the group consisting of plant polyphenols,
gardenia blue, cocoa pigment, purple sweet potato pigment, purple cabbage pigment, or algae blue pigment.

2. The product according to claim 1, wherein the quercetin derivative is rutin, polystachoside, neoisorutin, guaijaverin, or quercitroside.

3. The product according to claim 1, wherein the extract containing the quercetin or the derivative thereof is a sophora japonica flower extract or a sophora japonica flower-bud extract.

4. The product according to claim 1, wherein content of the natural dye substance accounts for 0.05-20% of a total weight of the product.

5. The product according to claim 1, wherein content of the natural dye substance accounts for 0.5-15% of a total weight of the product.

6. A combined product for human or animal hair dyeing, comprising:
a softening preparation;
a dye preparation; and
a mordant preparation,
wherein the dye preparation comprises effective amount of natural dye substances that comprises at least two kinds of substances and displays at least two color series;
wherein a new color is produced by a superposition of the at least two color series;
wherein at least one of the at least two kinds of substances displays a yellow or yellowish brown color series and is selected from the group consisting of quercetin or a derivative thereof, an extract containing quercetin or the derivative thereof, and a mixture thereof; and
wherein:
at least one of the at least two kinds of substances displays a color series other than the yellow or yellowish brown color series;
the color series other than the yellow or yellowish brown color series is a purple or purple-black color series, or a blue or blue-black color series;
the at least one of the at least two kinds of substances displaying the color series other than the yellow or yellowish brown color series is selected from the group consisting of plant polyphenols,
gardenia blue, cocoa pigment, purple sweet potato pigment, purple cabbage pigment, or algae blue pigment.

7. The combined product according to claim 6, wherein the quercetin derivative is rutin, polystachoside, neoisorutin, guaijaverin, or quercitroside.

8. The combined product according to claim 6, wherein the extract containing the quercetin or the derivative thereof is a sophora japonica flower extract or a sophora japonica flower-bud extract.

9. The combined product according to claim 6, wherein content of the natural dye substance accounts for 0.05-20% of a total weight of the combined product.

10. The combined product according to claim 6, characterized by at least one of the following:
the softening preparation comprises one or more of a disulfide bond reducing agent, a penetration enhancer, a thickener, and an alkalizer;
the dye preparation further comprises one or more of an antioxidant, a penetration enhancer, and preservative; and
the mordant preparation comprises one or more of an antioxidant, a penetration enhancer, and preservative.

11. The combined product according to claim 6, wherein the combined product is in a formulation selected from the group consisting of:
(1) a four-preparation type including the at least two kinds of substances in the dye preparation being divided into a dyeing component and a color-matching component according to the at least two color series such that the formulation of the combined product comprises the softening preparation, the dyeing component, the color-matching component, and the mordant preparation;
(2) a three-preparation type including the softening preparation, the dye preparation and the mordant preparation;

(3) a three-preparation type including the at least two kinds of substances in the dye preparation being divided into a dyeing component and a color-matching component according to the at least two color series such that the formulation of the combined product comprises the softening preparation and the mordant preparation combined with the dyeing component or the color-matching component; and (4) a two-preparation type including the dye preparation combined with the softening preparation or the mordant preparation.

12. A method of using the combined product according to claim 11, which is selected from the group consisting of:
   (1) the different preparations of each formulation are separately smeared on the human or animal hair and stay for a period of time between each preparation smearing;
   (2) some of the preparations and components of each formulation are mixed and smeared on the human or animal hair, then remaining preparations are separately smeared on the human or animal hair, and stay for a period of time between each preparation smearing; and
   (3) all the preparations of each formulation are mixed, then smeared on the human or animal hair and stay for a period of time.

13. A method for human or animal hair dyeing, the method comprises dyeing the human or animal hair with a product or combined product for human or animal hair dyeing that comprises effective amount of natural dye substances,
   wherein the natural dye substance comprises at least two kinds of substances and displays at least two color series;
   wherein a new color is produced by a superposition of the at least two color series; and
   wherein at least one of the at least two kinds of substances displays a yellow or yellowish brown color series and is selected from the group consisting of quercetin or a derivative thereof, an extract containing quercetin or the derivative thereof, and a mixture thereof and wherein:
   at least one of the at least two kinds of substances displays a color series other than the yellow or yellowish brown color series;
   the color series other than the yellow or yellowish brown color series is a purple or purple-black series, or blue or blue-black color series;
   the at least one of the at least two kinds of substances displaying the color series other than the yellow or yellowish brown color series is selected from the group consisting of plant polyphenols, gardenia blue, cocoa pigment, purple sweet potato pigment, purple cabbage pigment or algae blue pigment.

14. The method according to claim 13, wherein the quercetin derivative is rutin, polystachoside, neoisorutin, guaijaverin, or quercitroside.

15. The method according to claim 13, wherein the extract containing the quercetin or the derivative thereof is a sophora japonica flower extract or a sophora japonica flower-bud extract.

16. The method according to claim 13, wherein:
   at least one of the at least two kinds of substances displays a color series other than the yellow or yellowish brown color series;
   the color series other than the yellow or yellowish brown color series is a purple or purple-black color series, or a blue or blue-black color series;
   the at least one of the at least two kinds of substances displaying the color series other than the yellow or yellowish brown color series is selected from the group consisting of plant polyphenols and other natural dyes; and
   the other natural dyes are indigo or gardenia blue, cocoa pigment, purple sweet potato pigment, purple cabbage pigment, or algae blue pigment.

17. The method according to claim 13, wherein content of the natural dye substance accounts for 0.05-20% of a total weight of the product or the combined product.

18. The method according to claim 13, wherein content of the natural dye substance accounts for 0.5-15% of a total weight of the product or the combined product.

* * * * *